United States Patent
Bleisch et al.

(10) Patent No.: US 11,634,423 B2
(45) Date of Patent: Apr. 25, 2023

(54) SUBSTITUTED PYRAZOLO[1,5-A]PYRIMIDINES AS INHIBITORS OF INTERFERON SIGNALING

(71) Applicant: Eli Lilly and Company, Indianapolis, IN (US)

(72) Inventors: Thomas John Bleisch, Noblesville, IN (US); Zhaogen Chen, Carmel, IN (US); Theodore Curtis Jessop, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 167 days.

(21) Appl. No.: 17/168,399

(22) Filed: Feb. 5, 2021

(65) Prior Publication Data

US 2021/0253581 A1 Aug. 19, 2021

Related U.S. Application Data

(60) Provisional application No. 62/975,257, filed on Feb. 12, 2020.

(51) Int. Cl.
*A61K 31/519* (2006.01)
*C07D 487/04* (2006.01)

(52) U.S. Cl.
CPC .................. *C07D 487/04* (2013.01)

(58) Field of Classification Search
CPC ........................ A61K 31/519; C07D 487/04
USPC ........................................ 514/259.3; 544/281
See application file for complete search history.

(56) References Cited

U.S. PATENT DOCUMENTS

| | | |
|---|---|---|
| 7,557,110 B2 | 7/2009 | Kataoka et al. |
| 7,645,762 B2 | 1/2010 | Paruch et al. |
| 8,637,526 B2 | 1/2014 | Blaney et al. |
| 8,921,380 B2 | 12/2014 | Tanimoto et al. |
| 10,273,237 B2 | 4/2019 | Liu et al. |
| 2006/0089499 A1 | 4/2006 | Gebauer et al. |
| 2016/0304524 A1 | 10/2016 | Liu et al. |
| 2019/0031664 A1 | 1/2019 | Masse et al. |
| 2019/0225620 A1 | 7/2019 | Spergel et al. |

FOREIGN PATENT DOCUMENTS

| | | |
|---|---|---|
| WO | 2004/022561 A1 | 3/2004 |
| WO | 2004/026229 A2 | 4/2004 |
| WO | 2005/077954 A2 | 8/2005 |
| WO | 2010/051549 A1 | 5/2010 |
| WO | 2012/078855 A1 | 6/2012 |
| WO | 2017/087590 A1 | 5/2017 |
| WO | 2018/093968 A1 | 5/2018 |
| WO | 2019/023468 A1 | 1/2019 |
| WO | 2020/055636 A1 | 3/2020 |
| WO | 2020/081508 A1 | 4/2020 |
| WO | 2020/123225 A1 | 6/2020 |

OTHER PUBLICATIONS

Moslin, et al., "Identification of imidazo[1,2-b]pyridazine TYK2 pseudokinase ligands as potent and selective allosteric inhibitors of TYK2 signalling," MedChemComm, vol. 8(4), pp. 689-808 (Apr. 2017).
Novinson, et al., "Synthesis of Antifungal Properties of Certain 7-Alkylaminopyrazolo[1,5-a]pyrimidines," J Med Chem, vol. 20(2), pp. 296-299 (1977).
Shiota, et al., "Synthesis and Structure-Activity Relationship of a New Series of Potent Angiotensin II Receptor Antagonists: Pyrazolo[1,5-a]pyrimidine Derivatives," Chem Pharm Bull, vol. 47(7), pp. 928-938 (1999).

*Primary Examiner* — Douglas M Willis
(74) *Attorney, Agent, or Firm* — Robert D. Shereda

(57) ABSTRACT

The present invention provides a compound of Formula I:

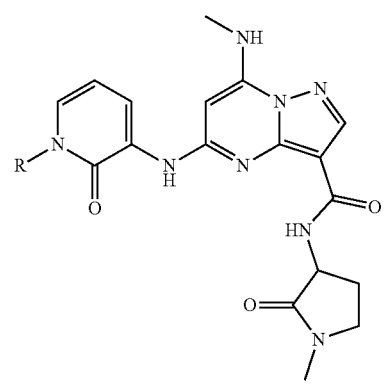

Formula I wherein R is

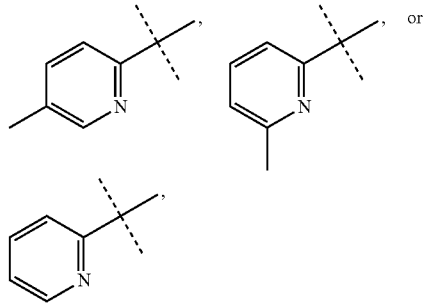

or a pharmaceutically acceptable salt thereof, useful for treating psoriasis, systemic lupus erythematosus, or type 1 diabetes.

19 Claims, No Drawings

SUBSTITUTED PYRAZOLO[1,5-A]PYRIMIDINES AS INHIBITORS OF INTERFERON SIGNALING

CROSS REFERENCE TO RELATED APPLICATIONS

The present application claims the benefit of, and priority to, U.S. Provisional Application No. 62/975,257, filed on Feb. 12, 2020, the entire contents of which are incorporated herein by reference.

BACKGROUND OF THE INVENTION

The present invention relates to novel compounds that bind to the pseudokinase domain (JH2) of TYK2 and inhibit certain cytokine signaling, in particular IL-23 and IFNα signaling, to pharmaceutical compositions comprising the compounds, to methods of using the compounds to treat certain autoimmune diseases and to intermediates and processes useful in the synthesis of the compounds.

Psoriasis and other autoimmune diseases, such as diabetes, are believed to be mediated by TYK2 signaling of certain proinflammatory cytokines (See e.g., J. S. Tokarski, et al., *J. Biol. Chem.*, vol. 290(17), pages 11061-11074 (2015); and, L. Marroqui, et al., *Diabetes*, vol. 64, pages 3808-3817 (2015)). Psoriasis is a chronic skin disease, which is estimated to affect approximately 2% of the general population. Treatment options for psoriasis include, for example, topical treatments, such as corticosteroids, phototherapy, such as ultraviolet B (UVB) light, and systemic treatments, such as methotrexate and apremilast. Unfortunately, such agents do not always provide effective treatment and can be associated with various untoward side effects.

US 2019/0031664 A1 discloses certain substituted pyrazolo[1,5-a]pyrimidines useful for treating various inflammatory and autoimmune disorders through inhibition of TYK2. U.S. Pat. No. 7,557,110 discloses certain pyrazolo[1,5-a]pyrimidine derivatives as kinase inhibitors useful for treating kinase mediated disorders, such as inflammatory disease and autoimmune disease.

There is a need for alternate treatments of autoimmune diseases, such as psoriasis, systemic lupus erythematosus (SLE), and diabetes. In particular, there is a need for compounds that bind to the TYK2 JH2 domain. In addition, there is a need for compounds that bind to the TYK2 JH2 domain and inhibit IL-23 and IFNα signal transduction.

BRIEF SUMMARY OF THE INVENTION

Accordingly, in one embodiment, the present invention provides a compound of Formula I:

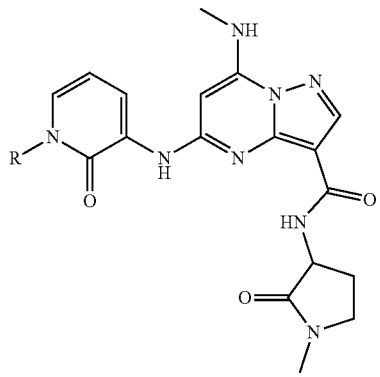

Formula I wherein R is

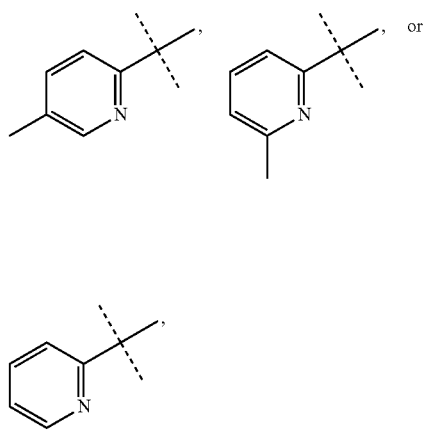

or a pharmaceutically acceptable salt thereof.

In a particular embodiment, the compound is of the Formula Ia:

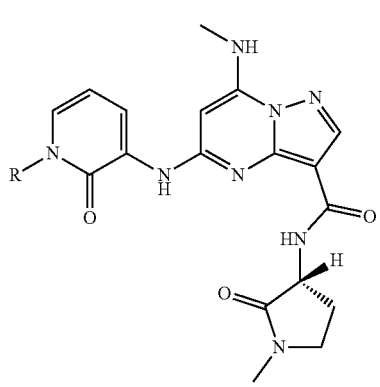

Formula Ia or a pharmaceutically acceptable salt thereof.

In a particular embodiment, the compound is of the Formula Ib:

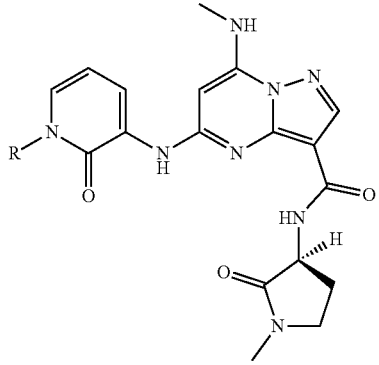

Formula Ib or a pharmaceutically acceptable salt thereof.

In an embodiment, R is:

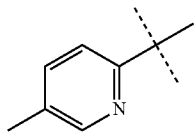

or a pharmaceutically acceptable salt thereof.

In an embodiment, R is:

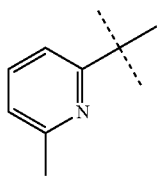

or a pharmaceutically acceptable salt thereof.

In an embodiment, R is:

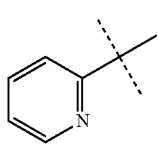

or a pharmaceutically acceptable salt thereof.

In an embodiment, the compound is:

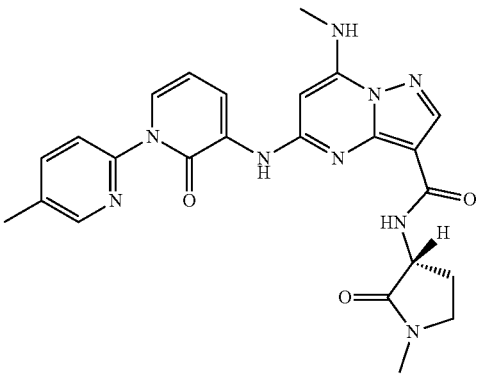 [SMILES: CNc1cc(Nc2cccn(-c3ccc(C)cn3)c2=O)nc2c(C(=O)N[C@@H]3CCN(C)C3=O)cnn12]

or a pharmaceutically acceptable salt thereof.

In an embodiment, the compound is:

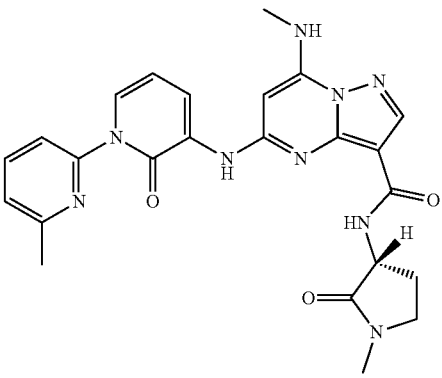 [SMILES: CNc1cc(Nc2cccn(-c3cccc(C)n3)c2=O)nc2c(C(=O)N[C@@H]3CCN(C)C3=O)cnn12]

or a pharmaceutically acceptable salt thereof.

In an embodiment, the compound is:

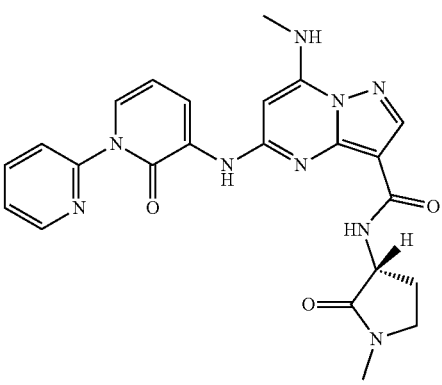 [SMILES: CNc1cc(Nc2cccn(-c3ccccn3)c2=O)nc2c(C(=O)N[C@@H]3CCN(C)C3=O)cnn12]

or a pharmaceutically acceptable salt thereof.

In an embodiment, the present invention also provides a method of treating psoriasis in a patient in need of such treatment, comprising administering to the patient an effective amount of a compound of Formula I, or a pharmaceutically acceptable salt thereof. In an embodiment, the present invention further provides a method of treating SLE in a patient in need of such treatment, comprising administering to the patient an effective amount of a compound of Formula I, or a pharmaceutically acceptable salt thereof. In an embodiment, the present invention further provides a method of treating a disease selected from the group consisting of inflammatory bowel disease, ulcerative colitis, Crohn's Disease, psoriatic arthritis, rheumatoid arthritis (RA), alopecia areata, atopic dermatitis, axial spondyloarthritis, multiple sclerosis (MS), type 1 diabetes, type 2 diabetes, and latent autoimmune diabetes of adults (LADA) in a patient in need of such treatment, comprising administering to the patient an effective amount of a compound of Formula I, or a pharmaceutically acceptable salt thereof.

In an embodiment, the present invention further provides a compound of Formula I, or a pharmaceutically acceptable salt thereof for use in therapy. In an embodiment, the present invention provides a compound of Formula I, or a pharmaceutically acceptable salt thereof for use in treating psoriasis. In an embodiment, the present invention provides a compound of Formula I, or a pharmaceutically acceptable salt thereof, for use in treating SLE. In an embodiment, the present invention also provides a compound of Formula I, or a pharmaceutically acceptable salt thereof, for use in treating a disease selected from the group consisting of inflammatory bowel disease, ulcerative colitis, Crohn's Disease, psoriatic arthritis, RA, alopecia areata, atopic dermatitis, axial spondyloarthritis, MS, type 1 diabetes, type 2 diabetes, and LADA.

In an embodiment, the present invention also provides the use of a compound of Formula I, or a pharmaceutically acceptable salt thereof, for the manufacture of a medicament for treating psoriasis. In an embodiment, the present invention provides the use of a compound of Formula I, or a pharmaceutically acceptable salt thereof, for the manufacture of a medicament for treating SLE. In an embodiment, the present invention also provides the use of a compound of Formula I, or a pharmaceutically acceptable salt thereof, for the manufacture of a medicament for treating a disease selected from the group consisting of inflammatory bowel disease, ulcerative colitis, Crohn's Disease, psoriatic arthritis, RA, alopecia areata, atopic dermatitis, axial spondyloarthritis, MS, type 1 diabetes, type 2 diabetes, and LADA.

In an embodiment, the present invention further provides a pharmaceutical composition, comprising a compound of Formula I, or a pharmaceutically acceptable salt thereof, with one or more pharmaceutically acceptable carriers, diluents, or excipients. In an embodiment, the present invention further provides a process for preparing a pharmaceutical composition, comprising admixing a compound of Formula I, or a pharmaceutically acceptable salt thereof, with one or more pharmaceutically acceptable carriers, diluents, or excipients. In an embodiment, the present invention also encompasses novel intermediates and processes for the synthesis of compounds of Formula I.

DETAILED DESCRIPTION OF THE INVENTION

As used herein, the terms "treating", "treatment", or "to treat" includes restraining, slowing, stopping, or reversing the progression or severity of an existing symptom or disorder.

As used herein, the term "patient" refers to a mammal, in particular a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be determined by one skilled in the art by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are formulated as pharmaceutical compositions administered by any route which makes the compound bioavailable. Most preferably, such compositions are for oral administration. Such pharmaceutical compositions and processes for preparing same are well known in the art (See, e.g., Remington: The Science and Practice of Pharmacy, L. V. Allen, Editor, $22^{nd}$ Edition, Pharmaceutical Press, 2012).

The compounds of Formula I, or a pharmaceutically acceptable salt thereof, are particularly useful in the treatment methods of the invention, with all configurations, including enantiomers, and mixtures thereof, including racemates, being contemplated within the scope of the invention. It is understood that these configurations are applicable both to the treatment methods and to the compounds of the invention.

Certain intermediates described in the following preparations may contain one or more nitrogen protecting groups. It is understood that protecting groups may be varied as appreciated by one of skill in the art depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

Individual isomers, including enantiomers, may be separated or resolved by one of ordinary skill in the art at any convenient point in the synthesis of compounds of the invention, by methods such as selective crystallization techniques or chiral chromatography (See, for example, J. Jacques, et al., "*Enantiomers, Racemates, and Resolutions*", John Wiley and Sons, Inc., 1981, and E. L. Eliel and S. H. Wilen," *Stereochemistry of Organic Compounds*", Wiley-Interscience, 1994).

A pharmaceutically acceptable salt of a compound of the invention can be formed, for example, by reaction of an appropriate free base of a compound of the invention, an appropriate pharmaceutically acceptable acid in a suitable solvent such as diethyl ether under standard conditions well known in the art. Additionally, the formation of such pharmaceutically acceptable salts can occur simultaneously upon deprotection of a nitrogen protecting group. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

Certain abbreviations are defined as follows: "BINAP" refers to (±)-2,2'-bis(diphenylphosphino)-1,1'-binaphthalene; "BOP" refers to (benzotriazol-1-yloxy)tris(dimethylamino)phosphonium hexafluorophosphate; "BrettPhos" refers to dicyclohexyl[3,6-dimethoxy-2',4',6'-tris(1-methylethyl)[1,1'-biphenyl]-2-yl]phosphine; "DCM" refers to dichloromethane; "DEM" refers to diethylmalonate; "DIEA" refers to N,N-diisopropylethylamine; "DMEM" refers to Dulbecco's Modified Eagle's Medium; "DMF" refers to N,N-dimethylformamide; "DMSO" refers to dimethyl sulfoxide; "EtOAc" refers to ethyl acetate; "EtOH" refers to ethanol and ethyl alcohol; "FBS" refers to Fetal Bovine Serum; "HATU" refers to 1-[bis(dimethylamino)methylene]-1H-1,2,3-triazolo[4,5-b]pyridinium 3-oxid hexafluorophosphate; "HEPES" refers to 4-(2-hydroxyethyl)-1-piperazineethanesulfonic acid; "HPLC" refers to high-performance liquid chromatography; "IFNα" refers to interferon alpha; "IL-2" refers to interleukin 2; "IL-23" refers to interleukin 23; "JAK" refers to Janus kinase; "LiHMDS" refers to lithium hexamethyldisilazide; "MeI" refers to methyl iodide; "MeNH$_2$" refers to methylamine; "MeOH" refers to methanol and methyl alcohol; "MTBE" refers to methyl tert-butyl ether; "NaOEt" refers to sodium ethoxide; "Pd-175 [tBuBrettPhos Pd(allyl)]OTf" refers to allyl(2-di-tert-butylphosphino-3,6-dimethoxy-2',4',6'-triisopropyl-1,1'-biphenyl)palladium(II) triflate; "RPM" refers to revolutions per minute; "RPMI" refers to Roswell Park Memorial Institute; "TEA" refers to triethylamine; "THF" refers to tetrahydrofuran; "TYK2" refers to tyrosine kinase 2; "UVB" refers to ultraviolet B; and "STAT" refers to signal transducer and activator of transcription protein.

The compounds of the present invention, or pharmaceutically acceptable salts thereof, may be prepared by a variety of procedures known to one of ordinary skill in the art, some of which are illustrated in the schemes, preparations, and examples below. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. Without limiting the scope of the invention, the following schemes, preparations, and examples are provided to further illustrate the invention.

Scheme 1

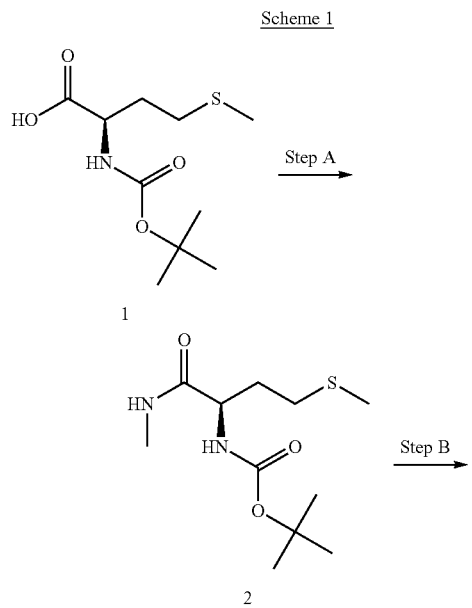

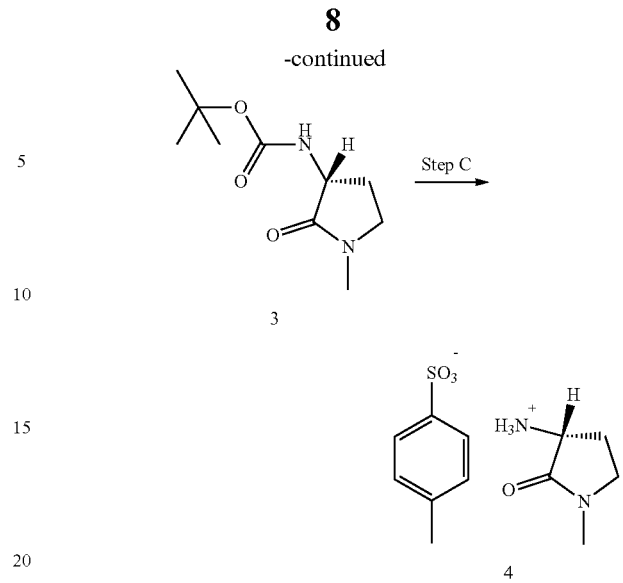

In scheme 1, step A, the formation of compound (2) is shown as an amide coupling under conditions well known in the art between compound (1) and MeNH$_2$ using a suitable organic base such as DIEA and a suitable coupling agent such as HATU in a solvent such as DMF at 0-22° C.

In step B, MeI is added to compound (2) to form a dimethylsulfonium iodide salt followed by treatment with a suitable base such as LiHMDS in a suitable solvent such as THF at 0-22° C. to give the cyclized compound (3).

In step C, compound (3) is deprotected under standard conditions using a suitable acid such as 4-methylbenzenesulfonic acid in a suitable solvent such as acetonitrile at around 55° C., followed by addition of a solvent such as MTBE to precipitate compound (4).

Scheme 2

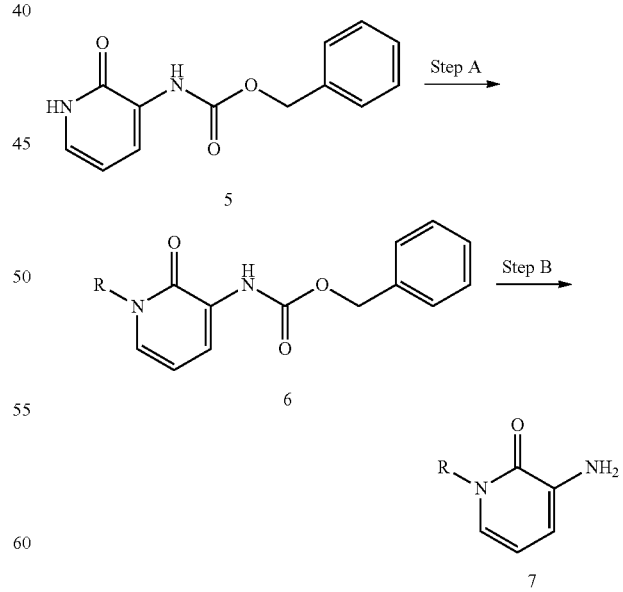

In scheme 2, step A, a Buchwald coupling is performed between compound (5) and a substituted bromopyridine using CuI with a suitable base such as potassium carbonate in suitable solvents such as DMF and 1,4-dioxane to give compound (6). In some cases, N',N'-dimethylethane-1,2-diamine is also added to the reaction mixture.

Step B depicts the deprotection of compound (6) through hydrogenation using a suitable catalyst such as 10% Pd/C or 20% Pd(OH)$_2$/C in a solvent such as EtOH or MeOH under a pressurized hydrogen atmosphere to give compound (7).

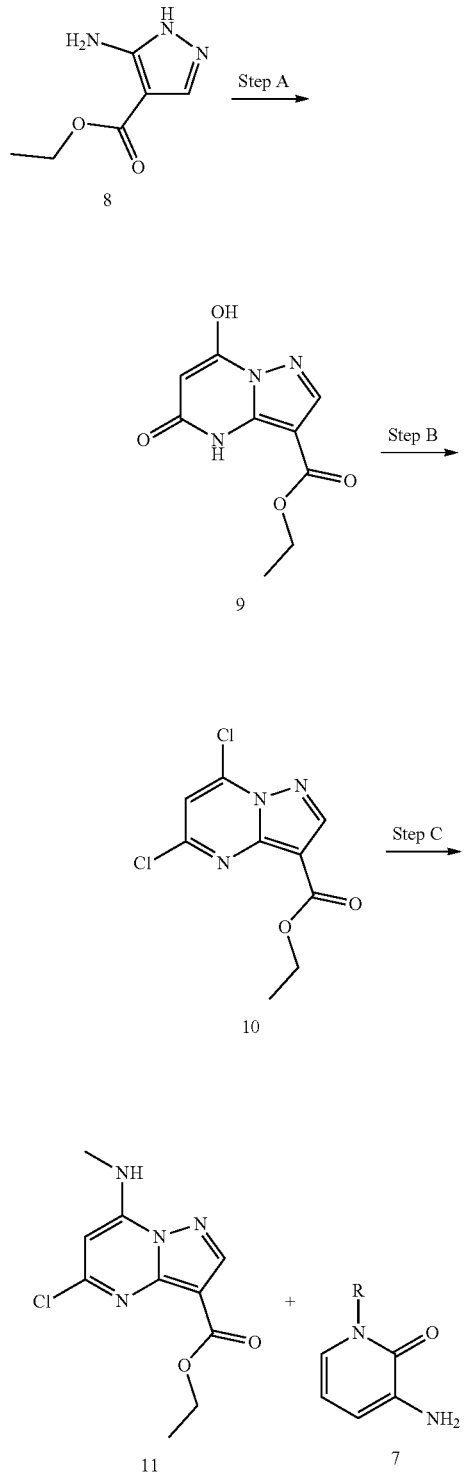

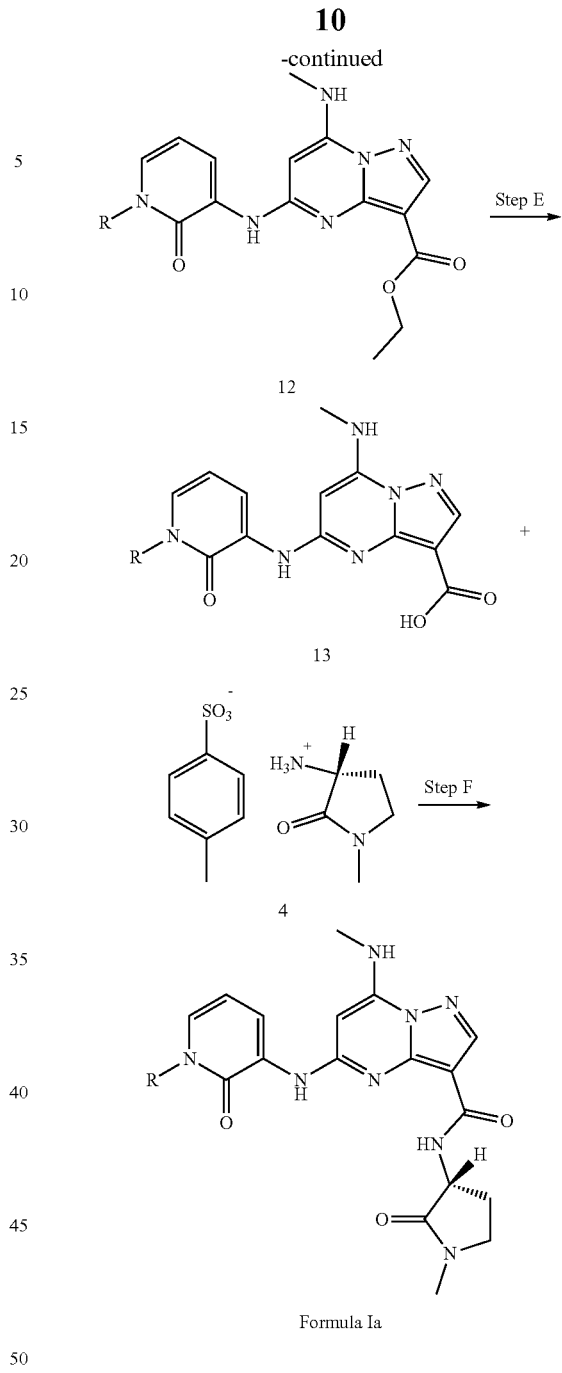

Scheme 3, step A depicts the addition of DEM to compound (8) and the subsequent cyclization to compound (9) using a suitable base such as NaOEt or potassium t-butoxide at around 80° C. in a solvent such as EtOH.

In step B, the 7-hydroxy and 5-oxo groups of compound (9) can be chlorinated using a suitable chlorine source such as POCl$_3$ and a suitable organic base such as pyridine at about 50-100° C. in a suitable solvent such as acetonitrile to give compound (10).

In step C, a selective nucleophilic aromatic substitution on the 7-chloro group of compound (10) can be performed under conditions well known in the art using an appropriate nucleophile such as MeNH$_2$ in a suitable solvent such as THF at ambient temperature to give compound (11).

In step D, a Buchwald coupling can be performed on compound (11) with compound (7) to form compound (12)

using a suitable catalyst and ligand system such as Pd-175 [tBuBrettPhos Pd(allyl)]OTf with a suitable base such as potassium acetate in an appropriate solvent such as 2-methyl-2-butanol with heating at 100° C.

Compound (12) can be treated with a suitable base such as aqueous LiOH in a suitable solvent system such as EtOH and THF at reflux to give compound (13) through basic hydrolysis of the ester as shown in step E.

Step F depicts the formation of the compound of Formula Ia through an amide coupling under conditions well known in the art between compound (13) and compound (4) using a suitable organic base such as DIEA and a suitable coupling agent such as BOP in a solvent such as DMF.

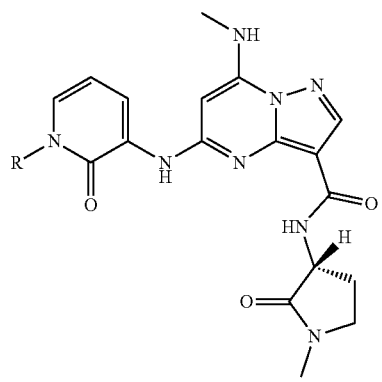

Formula Ia

Scheme 4

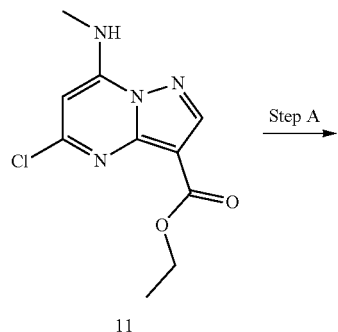

11

Scheme 4, step A depicts the basic hydrolysis of compound (11) with a suitable base such as aqueous NaOH in a solvent such as 1,4-dioxane at 50° C. to give compound (14).

Step B shows the amide coupling between compounds (14) and (15) using conditions generally described in Scheme 3, step F to give compound (16).

In step C, a Buchwald coupling can be performed between compounds (16) and (7) using a suitable catalyst and ligand system such as Pd-175 [tBuBrettPhos Pd(allyl)]OTf or allylpalladium(II) chloride dimer and BINAP with a suitable base such as potassium acetate in an appropriate solvent system such as 1,4-dioxane and 2-methyl-2-butanol with heating at 120-140° C. to give the compound of Formula Ia.

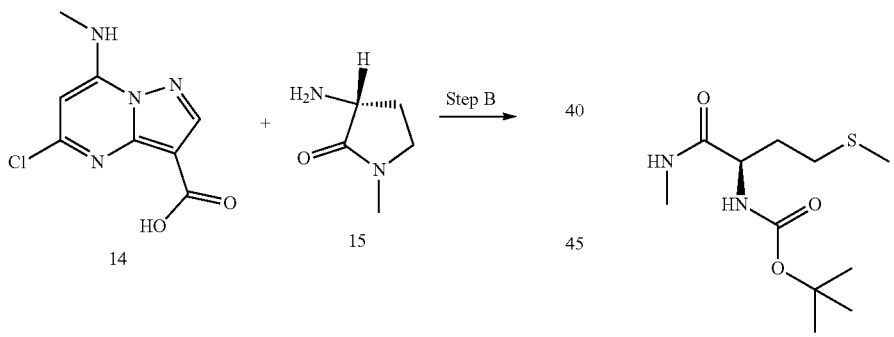

14

15

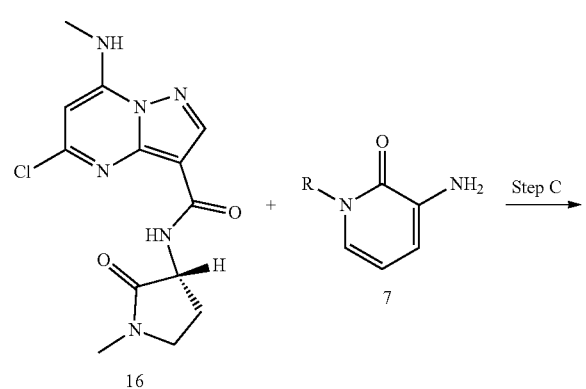

16

7

Scheme 1, step A: A solution of (tert-butoxycarbonyl)-D-methionine (400 g, 1.6 mol), methyl amine hydrochloride (162.47 g, 2.4 mol), and DIEA (700 mL, 4.01 mol) in DMF (4 L) is cooled to 0° C. and HATU (732.1 g, 1.92 mol) is added. The reaction is warmed to ambient temperature. After 2 hours stirring, the solvent is evaporated. Water (10 L) is then added and the aqueous solution is extracted with DCM (2×3 L). The organic layers are combined, washed with saturated aqueous sodium bicarbonate solution (3 L), dried over sodium sulfate, and concentrated in vacuo. The resulting residue is purified by silica gel chromatography eluting with EtOAc in hexane to give the title compound as a white solid (368 g, 87%). ES/MS m/z 263 (M+H).

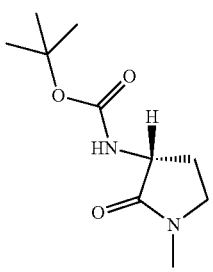

Scheme 1, step B: A mixture of tert-butyl N-[(1R)-1-(methylcarbamoyl)-3-methylsulfanyl-propyl]carbamate (368 g, 1.40 mol) and MeI (3.68 L, 59.11 mol) is stirred at ambient temperature for 18 hours. Then the mixture is concentrated in vacuo. A portion of the resulting crude dimethylsulfonium iodide salt (210 g, 0.52 mol) is dissolved in THF (4.7 L), cooled to 0° C. under a nitrogen atmosphere, and LiHMDS (1.00 M solution in THF, 1.16 L, 1.16 mol) is added dropwise. The reaction mixture is then warmed to ambient temperature. After 4 hours, water (2.4 L) is added and the solvent is concentrated to half volume. The mixture is extracted with DCM (2×3 L). The organics are combined and concentrated in vacuo. The residue is purified by silica gel chromatography eluting with MeOH in DCM to give the title compound as white solid (50 g). ES/MS m/z 215 (M+H). Chiral HPLC: Rt (retention time)=9.13 minutes; LC Column: ChiralPAc IA OD 4.6×250 mm 5 μm; isocratic: 0.1% diethyl amine/hexanes/ethanol (85/15); Column Temp: 25° C.; Flow Rate: 1.0 mL/min.

Optical rotation: $[\alpha]_D^{20}=+53°$ (C=0.5, MeOH).

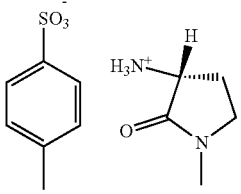

Scheme 1, step C: A mixture of tert-butyl N-[(3R)-1-methyl-2-oxo-pyrrolidin-3-yl]carbamate (46 g, 214.69 mmol) and 4-methylbenzenesulfonic acid (74.5 g, 433 mmol) in acetonitrile (500 mL) is heated at 55° C. and stirred for 4 hours. MTBE (1 L) is then added and the mixture is cooled to 22° C. The resulting solid is collected by filtration, washed with additional MTBE, and dried under vacuum to constant weight to give the title compound as a white solid (60 g, 95%). ES/MS m/z 115 (M+H).

Optical rotation: $[\alpha]_D^{20}=+31.3°$ (C=0.5, MeOH).

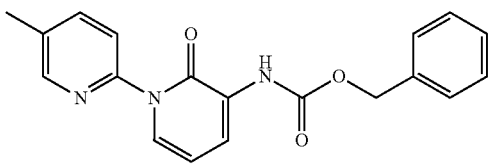 [SMILES: Cc1ccc(-n2cccc(NC(=O)OCc3ccccc3)c2=O)nc1]

Scheme 2, step A: A high pressure vessel is charged with benzyl N-(2-oxo-1H-pyridin-3-yl)carbamate (6 g, 24 mmol), cuprous iodide (0.9 g, 5 mmol), 2-bromo-5-methylpyridine (3.75 g, 21.4 mmol), potassium carbonate (7 g, 51 mmol), 1,4-dioxane (130 mL), and DMF (0.5 mL). The reaction is heated at 110° C. for 4 hours. The mixture is cooled to ambient temperature, filtered through diatomaceous earth, and washed with 1,4-dioxane. The filtrate is concentrated in vacuo to give a dark brown oil. The resulting residue is purified by silica gel flash chromatography eluting with 0-60% EtOAc/hexane over 25 minutes to give the title compound as a pale solid (5 g, 62%). ES/MS m/z 336 (M+H).

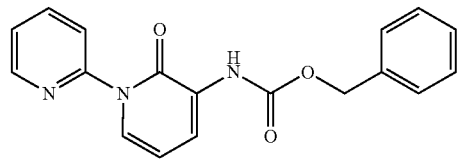 [SMILES: O=C(Nc1cccn(-c2ccccn2)c1=O)OCc1ccccc1]

Scheme 2, step A: A high pressure vessel is charged with benzyl N-(2-oxo-1H-pyridin-3-yl)carbamate (10.10 g, 41.36 mmol), cuprous iodide (1.6 g, 8.6 mmol), 2-bromopyridine (5.2 mL, 54 mmol), potassium carbonate (11.8 g, 86 mmol), 1,4-dioxane (200 mL), and N',N'-dimethylethane-1,2-diamine (2 mL, 17.4 mmol). The reaction is heated at 115° C. for 18 hours. The mixture is cooled to ambient temperature and filtered through diatomaceous earth. The filtrate is concentrated in vacuo to give a brown oil. The resulting residue is purified by silica gel flash chromatography eluting with 0-60% EtOAc/hexane over 30 minutes to give the title compound as a white solid (10.14 g, 76%). ES/MS m/z 322.0 (M+H).

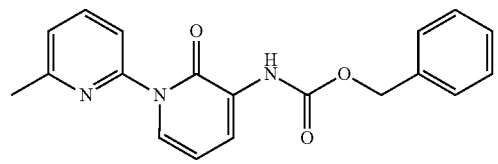 [SMILES: Cc1cccc(-n2cccc(NC(=O)OCc3ccccc3)c2=O)n1]

Scheme 2, step A: A high pressure vessel is charged with benzyl N-(2-oxo-1H-pyridin-3-yl)carbamate (9.8 g, 40 mmol), cuprous iodide (1.9 g, 10 mmol), 2-bromo-6-methylpyridine (5.9 mL, 51 mmol), potassium carbonate (11 g, 80 mmol), N',N'-dimethylethane-1,2-diamine (2 mL), and 1,4-dioxane (190 mL). The reaction is heated at 115° C. for 5 hours. The mixture is cooled to ambient temperature and filtered through diatomaceous earth. The filtrate is concentrated in vacuo to give a brown oil. The resulting residue is purified by silica gel flash chromatography eluting with 0-50% EtOAc/hexane over 30 minutes to give the title compound as a white solid (7.77 g, 58%). ES/MS m/z 336.0 (M+H).

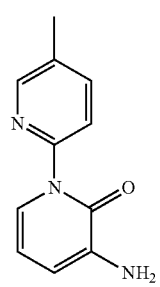

Scheme 2, step B: A Parr shaker is purged with nitrogen and charged with 10% Pd/C (1.27 g, 1.19 mmol). The Parr shaker is purged with nitrogen and then charged with MeOH (25 mL) and benzyl N-[1-(5-methyl-2-pyridyl)-2-oxo-3-pyridyl]carbamate (5.0 g, 15 mmol) dissolved in MeOH (25 mL) and EtOAc (10 mL). The Parr shaker is sealed, purged with nitrogen, then hydrogen, and pressurized to 138 kPa. The mixture is stirred at 30° C. for 20 minutes. The reaction mixture is filtered and the solvent concentrated in vacuo to give the title compound as a yellow solid (2.7 g, 90%). ES/MS m/z 202 (M+H).

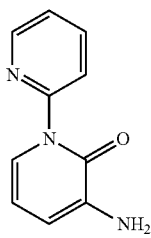

Scheme 2, step B: A Parr shaker is purged with nitrogen and charged with 20% Pd(OH)$_2$/C (5.7 g, 41 mmol). The Parr shaker is purged with nitrogen and then charged with EtOH (200 mL) and benzyl N-[2-oxo-1-(2-pyridyl)-3-pyridyl]carbamate (9.2 g, 29 mmol) dissolved in EtOH (200 mL). The Parr shaker is sealed, purged with nitrogen, then hydrogen, and pressurized to 48 kPa. The mixture is stirred at ambient temperature for 50 minutes. The reaction mixture is filtered and the solvent concentrated in vacuo to give the title compound as a yellow solid (5.3 g, 99%). ES/MS m/z 188.0 (M+H).

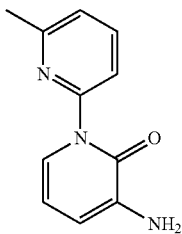

Scheme 2, step B: A Parr shaker purged with nitrogen is charged with 200% Pd(OH)$_2$/C (7.7 g, 55 mmol). The Parr shaker is purged with nitrogen and then charged with EtOH (200 mL) and benzyl N-[1-(6-methyl-2-pyridyl)-2-oxo-3-pyridyl]carbamate (7.77 g, 23 mmol) dissolved in EtOH (200 mL). The Parr shaker is sealed, purged with nitrogen, then hydrogen, and pressurized to 62 kPa. The mixture is stirred at ambient temperature for 55 minutes. The reaction mixture is filtered and the solvent concentrated in vacuo to a viscous oil. The crude material is suspended in DCM (40 mL) and hexane is added with stirring until a precipitate formed. The mixture is filtered and air dried to give the title compound as a tan solid (3.0 g, 51%). ES/MS m/z 202.0 (M+H).

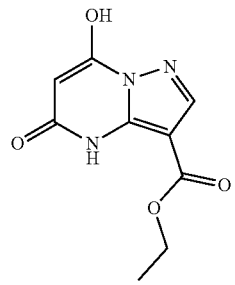 [SMILES: CCOC(=O)c1cnn2c(O)cc(=O)[nH]c12]

Scheme 3, step A: Ethyl 5-amino-1H-pyrazole-4-carboxylate (12.5 g, 80.6 mmol), and DEM (18.5 mL, 121 mmol) are dissolved in EtOH (90 mL). To this mixture is added NaOEt (21 mass % in EtOH, 45.1 mL, 121 mmol) and the reaction is stirred at 90° C. for 24 hours. After this time, the reaction is cooled to ambient temperature. The mixture is then made acidic with 5N HCl aqueous solution and the resulting precipitate is filtered to give the title compound as a white solid (11.7 g, 65.1%). ES/MS m/z 224 (M+H).

Alternate Preparation 10

Scheme 3, step A: To a solution of ethyl 5-amino-1H-pyrazole-4-carboxylate (400 g, 2.58 mol) and DEM (584 mL, 3.87 mol) in EtOH (6.00 L) is added potassium t-butoxide (578 g, 5.16 mol) at 25° C. under nitrogen. The solution is stirred at 80° C. for 12 hours and then the reaction is cooled to 22° C. The reaction mixture is diluted with 0.1N HCl (2 L) and the pH is adjusted to 3 with 5N HCl. The mixture is filtered and the filter cake is washed with water (800 mL). The solid is dried under vacuum to constant weight to give the title compound as an off-white solid (460 g, 81%). ES/MS m/z 224 (M+H).

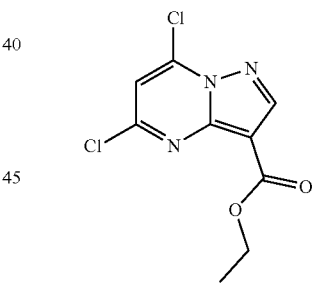

Scheme 3, step B: Ethyl 7-hydroxy-5-oxo-4H-pyrazolo[1,5-a]pyrimidine-3-carboxylate (11.7 g, 52.4 mmol) is suspended in acetonitrile (50 mL) and purged with nitrogen for 5 minutes. To this mixture is added POCl$_3$ (14.8 mL, 157 mmol) followed by pyridine (4.28 mL, 52.4 mmol) at 50° C. and then the reaction is stirred at 100° C. for 5 hours. After this time, the reaction is cooled to ambient temperature and poured into an ice/water mixture. This mixture is neutralized with saturated aqueous sodium bicarbonate solution and the resulting precipitate is filtered to give the title compound as a white solid (13 g, 95.3%). ES/MS m/z ($^{35}$Cl/$^{37}$Cl) 260/262 [M+H]$^+$.

Alternate Preparation 11

Scheme 3, step B: To a suspension of ethyl 7-hydroxy-5-oxo-4H-pyrazolo[1,5-a]pyrimidine-3-carboxylate (400 g, 1.79 mol) in acetonitrile (2 L), POCl₃ (416 mL, 4.48 mol) and pyridine (217 mL, 2.69 mol) are added drop-wise at 50° C. under nitrogen. The reaction is stirred at 80° C. for 12 hours. The reaction mixture is concentrated in vacuo and the residue is poured into water (2 L). The reaction mixture is filtered and the solid is washed with water (800 mL). The solid is dried under vacuum to constant weight to give the title compound as an orange solid (360 g, 66%). ES/MS m/z ($^{35}$Cl/$^{37}$Cl) 260/262 [M+H]⁺.

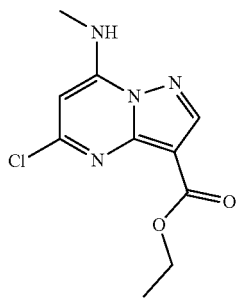 [SMILES: CCOC(=O)c1cnn2c(NC)cc(Cl)nc12]

Scheme 3, step C: Ethyl 5,7-dichloropyrazolo[1,5-a]pyrimidine-3-carboxylate (50.0 g, 192 mmol) is added to THF (250 mL) and the solution is cooled to 10° C. A solution of MeNH₂ (33% w/w in EtOH) (79 mL, 634 mmol) is then added, keeping the temperature below 20° C. The reaction mixture is stirred and warmed to 22° C. and stirred for 4 hours. Water (300 mL) is then added and the mixture is stirred for an additional 1 hour.

The resulting solids are collected by filtration and washed with a THF/water mixture (2:3) (100 mL) and water (400 mL). The solid is then dried under vacuum (10 mbar/50° C.) to constant weight to give the title compound as pale brown solid (49.5 g, 90%). ES/MS m/z ($^{35}$Cl/$^{37}$Cl) 255/257 [M+H]⁺.

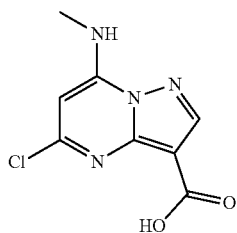

Scheme 4, step A: 1N NaOH (50 mL, 50 mmol) is added to ethyl 5-chloro-7-(methylamino)pyrazolo[1,5-a]pyrimidine-3-carboxylate (9.05 g, 35.5 mmol) in 1,4-dioxane (50 mL) and the mixture is warmed to 50° C. After 16 hours, the mixture is cooled to ambient temperature and the pH is adjusted to ~3 by addition of 1N HCl. The resulting solid is collected and dried under vacuum to give the title compound as a light tan solid (8.0 g, >99%). ES/MS m/z ($^{35}$Cl/$^{37}$Cl) 227/229 [M+H]⁺.

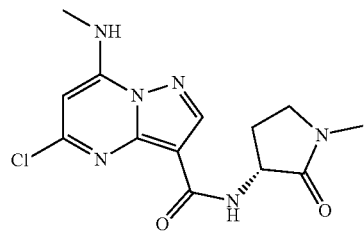 [SMILES: CNc1cc(Cl)nc2c(C(=O)N[C@@H]3CCN(C)C3=O)cnn12]

Scheme 4, step B: To a mixture of 5-chloro-7-(methylamino)pyrazolo[1,5-a]pyrimidine-3-carboxylic acid (4.3 g, 19 mmol) and (R)-3-amino-1-methyl-pyrrolindin-2-one (2.4 g, 21 mmol) in DMF (95 mL) is added DIEA (14 mL, 80 mmol) and BOP (11 g, 24 mmol). The mixture is stirred at ambient temperature for 2 hours and then quenched with water resulting in the formation of an off-white solid. The resulting solid is filtered and dried under vacuum at ambient temperature to give the title compound as an off-white solid (5 g, 82%). ES/MS m/z 323 (M+H).

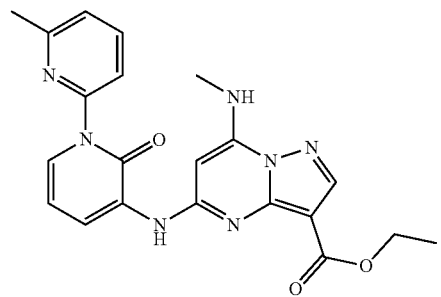 [SMILES: CCOC(=O)c1cnn2c(NC)cc(Nc3cccn(-c4cccc(C)n4)c3=O)nc12]

Scheme 3, step D: A round bottom flask is charged with ethyl 5-chloro-7-(methylamino)pyrazolo[1,5-a]pyrimidine-3-carboxylate (2 g, 7.8 mmol), potassium acetate (2.2 g, 15.7 mmol), and 2-methylbutan-2-ol (25 mL). The flask is flushed with nitrogen for 5 minutes. Pd-175 [tBuBrettPhos Pd(allyl)]OTf (184 mg, 0.24 mmol) and acetic acid (0.045 mL, 0.79 mmol) are added. The mixture is heated at 100° C. for 18 hours. The mixture is then cooled to ambient temperature and diluted with DCM/water (30 mL). The mixture is filtered and dried under vacuum at ambient temperature to give the title compound (2.4 g, 73%). ES/MS m/z 420.0 (M+H).

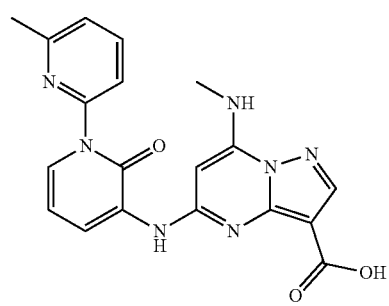 [SMILES: CNc1cc(Nc2cccn(-c3cccc(C)n3)c2=O)nc2c(C(=O)O)cnn12]

Scheme 3, step E: A round bottom flask is charged with ethyl 7-(methylamino)-5-[[1-(6-methyl-2-pyridyl)-2-oxo-3-pyridyl]amino]pyrazolo[1,5-a]pyrimidine-3-carboxylate (2.4 g, 5.7 mmol), EtOH (20 mL), and lithium hydroxide (0.34 g, 4.1 mmol) dissolved in water (12 mL). The mixture is heated to reflux under nitrogen for 18 hours and then allowed to cool to ambient temperature. The pH is adjusted to ~2 by addition of 1N HCl. After stirring for 30 minutes, the resulting solid is filtered, washed with ice cold water (20 mL), and dried under vacuum at ambient temperature to give the title compound (1.6 g, 71%). ES/MS m/z 392.0 (M+H).

Preparation 17

Preparation of the Tracer for the TYK2-JH2 Tracer Binding Assay (2E)-2-[(2E,4E)-5-[3-[6-[4-[4-[[5-[2-Methoxy-3-(1-methyl-1,2,4-triazol-3-yl)anilino]-6-(methylcarbamoyl)-1,2,4-triazin-3-yl]amino]pyrazol-1-yl]-1-piperidyl]-6-oxo-hexyl]-3-methyl-5-sulfonato-1-(3-sulfonatopropyl)indol-1-ium-2-yl]penta-2,4-dienylidene]-3,3-dimethyl-1-(3-sulfonatopropyl)indoline-5-sulfonate; triethylammonium 2-Methoxy-3-(1-methyl-1,2,4-triazol-3-yl)aniline (5.95 g, 29.1 mmol) is added to ethyl 5-chloro-3-methylsulfanyl-1,2,4-triazine-6-carboxylate (6.8 g, 29.0 mmol) in NMP (20 mL) and stirred at ambient temperature. After 90 minutes, diethyl ether (100 mL) is added and the mixture is stirred for 15 minutes. The resulting solid is filtered and washed with diethyl ether. The solid is partitioned between DCM and saturated aqueous sodium bicarbonate solution. The organic layer is further washed with saturated aqueous sodium chloride solution, dried over sodium sulfate, filtered, and evaporated to give ethyl 5-[2-methoxy-3-(1-methyl-1,2,4-triazol-3-yl)anilino]-3-methylsulfanyl-1,2,4-triazine-6-carboxylate as a faint yellow solid (10.12 g, 82%). ES/MS m/z 402.2 (M+H).

Ethyl 5-[2-methoxy-3-(1-methyl-1,2,4-triazol-3-yl)anilino]-3-methylsulfanyl-1,2,4-triazine-6-carboxylate (10.12 g, 23.7 mmol) is stirred in 2M MeNH$_2$ in THF (75 mL, 150 mmol) at ambient temperature for 4 hours. Diethyl ether (100 mL) is added and the mixture is stirred for 15 minutes. The resulting solid is collected, washed with diethyl ether (50 mL), and dried under vacuum to give 5-[2-methoxy-3-(1-methyl-1,2,4-triazol-3-yl)anilino]-N-methyl-3-methylsulfanyl-1,2,4-triazine-6-carboxamide as a light yellow solid (8.03 g, 78%). ES/MS m/z 387.0 (M+H).

m-Chloroperoxybenzoic acid (703 mg, 3.14 mmol) is added to a suspension of 5-[2-methoxy-3-(1-methyl-1,2,4-triazol-3-yl)anilino]-N-methyl-3-methylsulfanyl-1,2,4-triazine-6-carboxamide (500 mg, 1.26 mmol) in DMF (12.5 mL) at 0° C. and allowed to warm to ambient temperature. After 30 minutes, tert-butyl 4-(4-aminopyrazol-1-yl)piperidine-1-carboxylate (520 mg, 1.89 mmol) is added and the mixture is stirred at ambient temperature. After 24 hours, the mixture is partitioned between DCM and saturated aqueous sodium bicarbonate solution. The organic layer is dried over magnesium sulfate, filtered, and evaporated. The resulting solid is triturated several times with diethyl ether and dried under vacuum to give tert-butyl 4-[4-[[5-[2-methoxy-3-(1-methyl-1,2,4-triazol-3-yl)anilino]-6-(methylcarbamoyl)-1,2,4-triazin-3-yl]amino]pyrazol-1-yl]piperidine-1-carboxylate as an 86% pure yellow solid (720 mg, 81%). ES/MS m z 605.2 (M+H).

4N HCl in dioxane (2.5 mL, 10 mmol) is added to a suspension of tert-butyl 4-[4-[[5-[2-methoxy-3-(1-methyl-1,2,4-triazol-3-yl)anilino]-6-(methylcarbamoyl)-1,2,4-triazin-3-yl]amino]pyrazol-1-yl]piperidine-1-carboxylate (720 mg, 1.0 mmol) in MeOH (5 mL) and stirred at ambient temperature. After 72 hours, the mixture is evaporated. The resulting material is partitioned between DCM (100 mL) and water (20 mL). The pH of the aqueous layer is adjusted to >8 by addition of 1N NaOH and extracted with 3:1 chloroform/isopropanol. The organic layers are combined, dried over magnesium sulfate, filtered, and evaporated. The resulting solid is triturated with diethyl ether and then dried under vacuum to give 5-[2-methoxy-3-(1-methyl-1,2,4-triazol-3-yl)anilino]-N-methyl-3-[[1-(4-piperidyl)pyrazol-4-yl]amino]-1,2,4-triazine-6-carboxamide as an 86% pure yellow solid (585 mg, 97%). ES/MS m/z 505.0 (M+H).

A solution of (2E)-2-[(2E,4E)-5-[3-[6-(2,5-dioxopyrrolidin-1-yl)oxy-6-oxo-hexyl]-3-methyl-5-sulfonato-1-(3-sulfonatopropyl)indol-1-ium-2-yl]penta-2,4-dienylidene]-3,3-dimethyl-1-(3-sulfonatopropyl)indoline-5-sulfonate triethylammonium (10 mg, 0.008 mmol) in DMSO (1 mL) is added to a solution of 5-[2-methoxy-3-(1-methyl-1,2,4-triazol-3-yl)anilino]-N-methyl-3-[[1-(4-piperidyl)pyrazol-4-yl]amino]-1,2,4-triazine-6-carboxamide (4.5 mg, 0.008 mmol) and TEA (0.002 mL, 0.014 mmol) in DMSO (1 mL). The reaction vial is wrapped in aluminum foil to protect from light and stirred at ambient temperature overnight. The resulting residue is purified by prep HPLC (Kinetix EVO C18 30 mm×100 mm, Sum) eluting with 0 to 20% acetonitrile in water to give the title compound as a bright blue solid (8.5 mg, 65%). ES/MS m/z 673.4 (M+H).

Example 1

7-(Methylamino)-N-[(3R)-1-methyl-2-oxo-pyrrolidin-3-yl]-5-[[1-(5-methyl-2-pyridyl)-2-oxo-3-pyridyl]amino]pyrazolo[1,5-a]pyrimidine-3-carboxamide

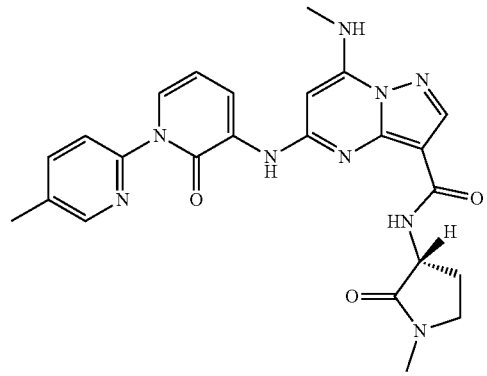 [SMILES: CNc1cc(Nc2cccn(-c3ccc(C)cn3)c2=O)nc2c(C(=O)N[C@@H]3CCN(C)C3=O)cnn12]

Scheme 4, step C: A microwave vessel is charged with 5-chloro-7-(methylamino)-N-[(3R)-1-methyl-2-oxo-pyrrolidin-3-yl]pyrazolo[1,5-a]pyrimidine-3-carboxamide (76 mg, 0.23 mmol), 3-amino-1-(5-methyl-2-pyridyl)pyridin-2-one (72 mg, 0.359 mmol), potassium acetate (48 mg, 0.47 mmol), 2-methylbutan-2-ol (0.8 mL), and 1,4-dioxane (0.8 mL). The flask is flushed with nitrogen for 5 minutes. BINAP (59 mg, 0.093 mmol) and allylpalladium(II) chloride dimer (16.7 mg, 0.0447 mmol) are added. The vessel is heated in a microwave at 120° C. After 20 minutes, the mixture is cooled to ambient temperature and filtered through diatomaceous earth. The resulting residue is purified via reverse phase chromatography to give the title compound (87 mg, 75%). ES/MS m/z 488.2 (M+H).

Example 2

7-(Methylamino)-N-[(3R)-1-methyl-2-oxo-pyrrolidin-3-yl]-5-[[1-(6-methyl-2-pyridyl)-2-oxo-3-pyridyl]amino]pyrazolo[1,5-a]pyrimidine-3-carboxamide

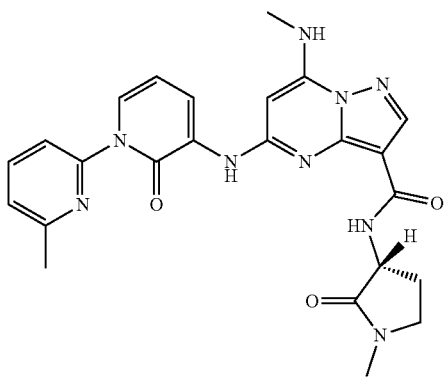

Scheme 3, step F: To a mixture of 7-(methylamino)-5-[[1-(6-methyl-2-pyridyl)-2-oxo-3-pyridyl]amino]pyrazolo[1,5-a]pyrimidine-3-carboxylic acid (1.2 g, 3.1 mmol) and (3R)-3-amino-1-methyl-pyrrolidin-2-one;4-methylbenzenesulfonic acid (0.9 g, 3 mmol) in DMF (15 mL) is added DIEA (2.1 mL, 12 mmol) and BOP (1.8 g, 3.9 mmol). After stirring at ambient temperature for 1 hour, the reaction mixture is added to water (240 mL) and the pH adjusted to ~6-7. After stirring for 30 minutes, the resulting solid is filtered, washed with ice cold water (20 mL), and dried under vacuum at ambient temperature. The resulting residue is purified via reverse phase chromatography and recrystallized from MeOH to give the title compound (446 mg, 30%). ES/MS m/z 488.2 (M+H).

Example 3

7-(Methylamino)-N-[(3R)-1-methyl-2-oxo-pyrrolidin-3-yl]-5-[[2-oxo-1-(2-pyridyl)-3-pyridyl]amino]pyrazolo[1,5-a]pyrimidine-3-carboxamide

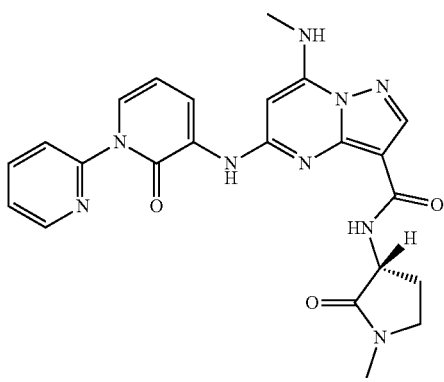 [SMILES: CNc1cc(Nc2cccn(-c3ccccn3)c2=O)nc2c(C(=O)N[C@@H]3CCN(C)C3=O)cnn12]

Scheme 4, step C: A microwave vessel is charged with 5-chloro-7-(methylamino)-N-[(3R)-1-methyl-2-oxo-pyrrolidin-3-yl]pyrazolo[1,5-a]pyrimidine-3-carboxamide (0.302 g, 0.935 mmol), 3-amino-1-(2-pyridyl)pyridin-2-one (0.21 g, 1.1 mmol), potassium acetate (281 mg, 2.7 mmol), 2-methylbutan-2-ol (7.5 mL), and 1,4-dioxane (7.5 mL). The flask is flushed with nitrogen for 5 minutes. Pd-175 [tBuBrettPhos Pd(allyl)]OTf (30 mg, 0.038 mmol) is added. The vessel is heated in a microwave at 140° C. After 40 minutes, the mixture is cooled to ambient temperature and filtered through diatomaceous earth. The resulting residue is purified via reverse phase chromatography to give the title compound (265 mg, 60%). ES/MS (m/z): 474.2 (M+H).

TYK2-JH2 Tracer Binding Assay

The pseudokinase domain (JH2) of human JAK (Janus family of cytoplasmic tyrosine kinases) family tyrosine kinase 2 (TYK2) (Genbank NP_003322) with an N-terminal His6 tag is expressed in baculovirus and purified by HisPur Ni-NTA affinity and Superdex 200 size-exclusion chromatography. The compound prepared in Preparation 17, a conjugate of Alexa Fluor 647 dye (Thermo Fisher Scientific) and a suitable TYK2 JH2 binder, is referred to herein as "the Tracer". A 3 fold, 10 point serial dilution of compound (Examples 1, 2, and 3) are prepared in 100% DMSO and 50 nL/well transferred to a Proxiplate-384F white plate (PerkinElmer 6008280) using acoustic liquid handling. Control wells used to determine percent inhibition contained 100% DMSO (50 nL) and either assay buffer containing the Tracer (2.00 nM final concentration) (min, low FRET) or diluted TYK2-JH2 enzyme (0.200 nM final concentration) and the Tracer (2.00 nM final concentration) (max, high FRET).

5.0 μL of His-tagged TYK2-JH2 (0.402 nM) and LanthaScreen Eu-anti-HIS Ab (4.02 nM, LifeTech, PV5597) in assay buffer (50 mM HEPES pH 75, 10 mM magnesium chloride, 1 mM ethylene glycol-bis(β-aminoethyl ether)-N,N,N',N'-tetraacetic acid, 0.01% Brij-35 and Milli-Q) water is added to the Proxiplate-384 plate containing the 50 nL of diluted compound and control wells. 5.0 μL of the Tracer (2.00 nM final concentration) in assay buffer is added to the plate and allowed to equilibrate for 30 minutes at ambient temperature. After 30 minutes, the plate is counted on a PerkinElmer Envision with the following settings: Excitation (340 nm), Tracer Emission (665 nm) and LanthaScreen Eu-anti-His Antibody Emission (615 nm). The ratio of Tracer Emission (665 nm) over LanthaScreen Eu-anti-His Antibody Emission (615 nm) is determined. Percent inhibition of ratio at each inhibitor concentration is calculated using the max and min control wells and fit to the four parameter nonlinear logistic equation in GeneData Screener® to give an $IC_{50}$ for the compounds tested. The data described in Table 1 demonstrates that the compounds of Examples 1-3 bind to the TYK2-JH2 pseudo kinase domain in vitro.

TABLE 1

| $IC_{50}$ values provided for Examples 1-3 | |
|---|---|
| Compound | TYK2-JH2 binding (nM) |
| Example 1 | <0.254 (n = 4) |
| Example 2 | <0.254 (n = 1) |
| Example 3 | <0.254 (n = 3) |

Inhibition of IFNα Signaling Through pSTAT1 in TF1 Cells

TF1 cells (ATCC, CL-2003) are grown in RPMI 1640 (GIBCO) supplemented with 10% dialyzed FBS, 0.1 mg/mL Ampicillin and 2 ng/mL granulocyte macrophage colony stimulating factor. TF1 cells (100 K per well) are seeded in a 96-well poly-D-lysine coated plates in serum-free DMEM and incubated overnight at 37° C. under 5% $CO_2$. Example 1 is serially diluted in DMSO, added to the cells, and incubated at 37° C. for 1 hour. Cells are then stimulated with 10 ng/mL IFNα2 at 37° C. for 20 minutes. After removing the medium, the cells are lysed in buffer containing Halt protease and phosphatase inhibitor cocktail (Thermo Scientific #78441) at ambient temperature for 30 minutes. The amount of p-Stat1 (Tyr701) is quantified as light emission at 615 nm using the AlphaLISA SureFire Ultra p-Stat1 (Tyr701) assay kit (Perkin Elmer #ALSU-PST1-A50K) following the vendor's recommended protocol. Percent inhibition at each inhibitor concentration is calculated and fit to the four parameter nonlinear logistic equation using Genedata Screener© to give an $IC_{50}$ for the compounds tested expressed as GeoMetric means with the standard error of the mean (SEM). The data described in Table 2 demonstrates that the compounds of Examples 1-3 are inhibitors of IFNα signaling through pSTAT1 in TF1 cells.

TABLE 2

| $IC_{50}$ values provided for Examples 1-3 | |
|---|---|
| Compound | IFNα inh (μM) |
| Example 1 | 0.112 (±0.055 μM, n = 4) |
| Example 2 | 0.206 (±0.065 μM, n = 3) |
| Example 3 | 0.106 (±0.070 μM, n = 3) |

IL23 pSTAT3 AlphaLISA Assay

IL-2-dependent Kit225 cells (University of Texas MD Anderson Cancer Center) expressing endogenous IL-23 receptors are stably transduced with the Lenti STAT3 Reporter linked to firefly luciferase (SABiosciences CLS-6028L). These cells are used to monitor TYK2 activity by quantifying gene expression caused by STAT3 phosporylation following induction by IL-23 in the presence of IL-2 using AlphaLISA technology (TGR Biosciences ALSU-TST3-A50K). The cells are grown in RPMI 1640 (Gibco 22400) supplemented with 10% FBS (Invitrogen 10082), 1× Pen/Strep (Gibco 15140-122), 200 ng/ml Puromycin (Sigma P9620), and fresh 10 ng/ml recombinant human IL-2 (R&D Systems 202-IL-50).

For assay preparation, cells are dispensed into Biocoat black poly-d-lysine coated clear bottom 384-well plates (Becton Dickinson Bio-Coat 35-4640) in DMEM (Sigma D5796) at 300,000 cells/well and allowed to incubate overnight at 37° C. Compounds solubilized in DMSO are serially diluted 1:3 to produce a 10-point concentration response curve (final DMSO=0.1%). Cells are pre-incubated with Example 1 for 1 hour at 37° C., then stimulated with IL-23 (25 ng/mL final) for 30 minutes. After centrifugation at 2000 rpm for 10 minutes, cell pellets are lysed with a mixture of 1:1 lysis buffer (TGR Biosciences) and Halt Protease & Phosphatase inhibitor cocktail (Thermo Scientific 1861281) for 30 minutes. The AlphaLISA reaction is performed following the vendor's recommended protocol, and the luciferase levels are measured using an Envision plate reader (Perkin Elmer). The relative $IC_{50}$ is calculated using a 4-parameter nonlinear logistic equation (GeneData Screener 13.0.5) to give an $IC_{50}$ for the compounds tested expressed as GeoMetric means with the standard error of the mean (SEM). The data described in Table 3 demonstrates that the compounds of Examples 1-3 are inhibitors of IL-23 signaling in a cell-based assay.

TABLE 3

| $IC_{50}$ values provided for Examples 1-3 | |
|---|---|
| Compound | IL-23 inh (μM) |
| Example 1 | 0.065 (±0.011 μM, n = 4) |
| Example 2 | 0.101 (±0.0005 μM, n = 2) |
| Example 3 | 0.101 (±0.022 μM, n = 3) |

We claim:

1. A compound of Formula I:

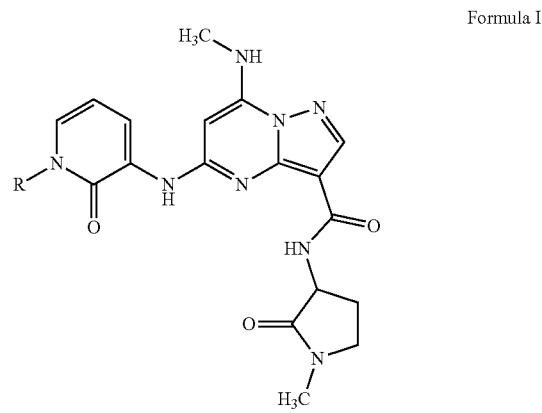

Formula I or a pharmaceutically acceptable salt or stereoisomer thereof, wherein:

R is:

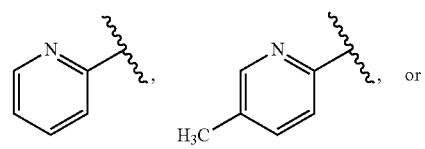

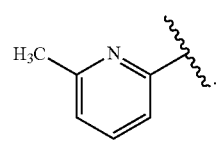

2. The compound according to claim 1, or the stereoisomer thereof, wherein the stereoisomer of the compound is of Formula Ia:

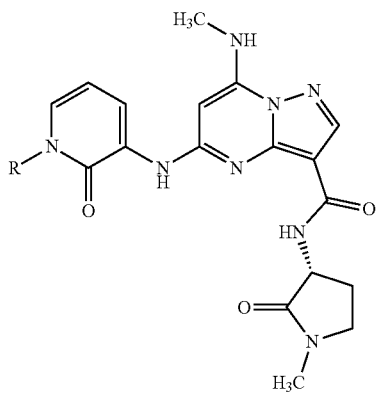

Formula Ia or a pharmaceutically acceptable salt thereof.

3. The compound according to claim 1, or a pharmaceutically acceptable salt or stereoisomer thereof, wherein R is:

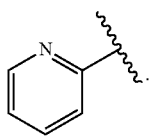

4. The compound according to claim 1, or a pharmaceutically acceptable salt or stereoisomer thereof, wherein R is:

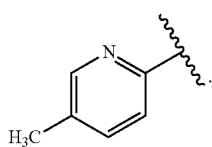

5. The compound according to claim 1, or a pharmaceutically acceptable salt or stereoisomer thereof, wherein R is:

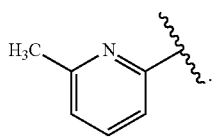

6. The compound according to claim 1, or the stereoisomer thereof, wherein the stereoisomer of the compound is:

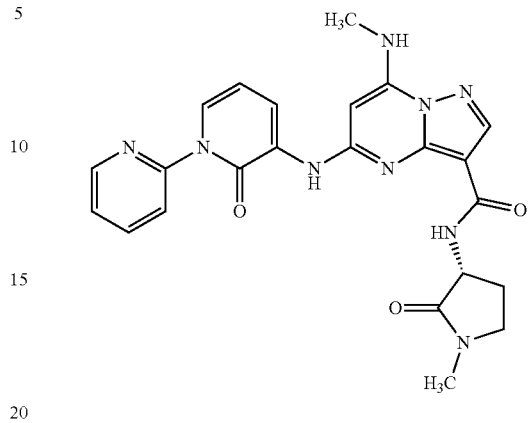

or a pharmaceutically acceptable salt thereof.

7. The compound according to claim 6, wherein the stereoisomer of the compound is:

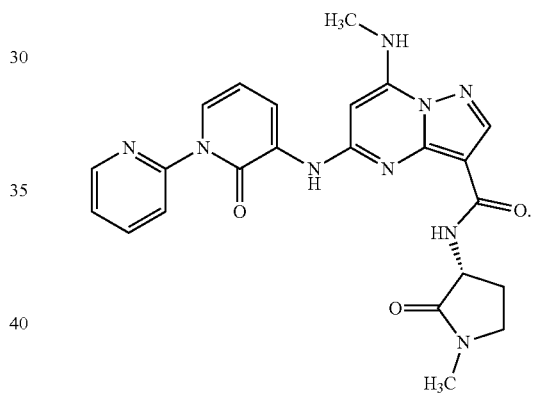

8. The compound according to claim 1, or the stereoisomer thereof, wherein the stereoisomer of the compound is:

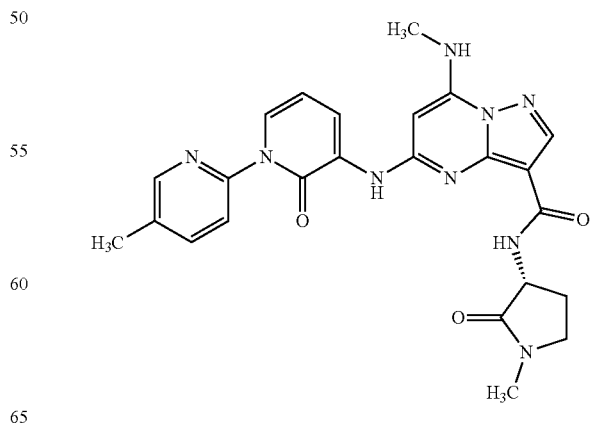

or a pharmaceutically acceptable salt thereof.

9. The compound according to claim 8, wherein the stereoisomer of the compound is:

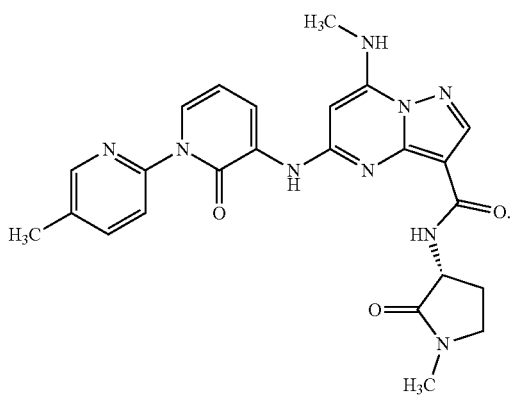 [SMILES: CNc1cc(Nc2cccn(-c3ccc(C)cn3)c2=O)nc2c(C(=O)N[C@@H]3CCN(C)C3=O)cnn12]

10. The compound according to claim 1, or the stereoisomer thereof, wherein the stereoisomer of the compound is:

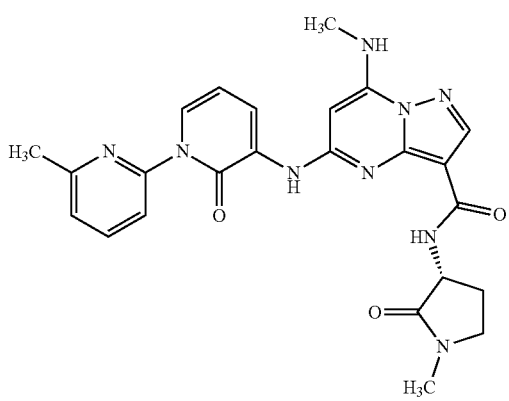 [SMILES: CNc1cc(Nc2cccn(-c3cccc(C)n3)c2=O)nc2c(C(=O)N[C@@H]3CCN(C)C3=O)cnn12]

or a pharmaceutically acceptable salt thereof.

11. The compound according to claim 10, wherein the stereoisomer of the compound is:

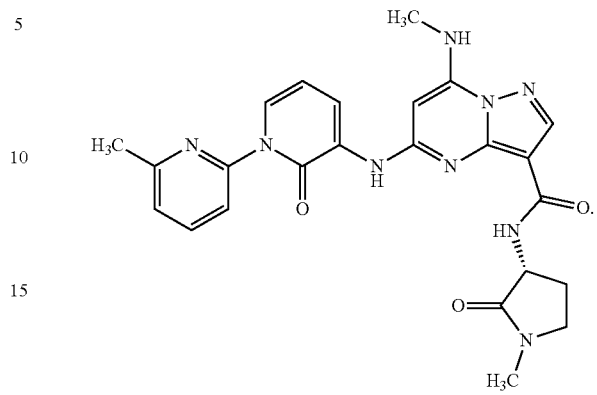

12. A pharmaceutical composition comprising one or more pharmaceutically acceptable carriers, diluents, or excipients and a compound according to claim 1, or a pharmaceutically acceptable salt or stereoisomer thereof.

13. A pharmaceutical composition comprising one or more pharmaceutically acceptable carriers, diluents, or excipients and the stereoisomer of the compound according to claim 8, or a pharmaceutically acceptable salt thereof.

14. A method for treating psoriasis in a patient, wherein the method comprises administering to the patient in need of such treatment an effective amount of a compound according to claim 1, or a pharmaceutically acceptable salt or stereoisomer thereof.

15. A method for treating psoriasis in a patient, wherein the method comprises administering to the patient in need of such treatment an effective amount of the stereoisomer of the compound according to claim 8, or a pharmaceutically acceptable salt thereof.

16. A method for treating systemic lupus erythematosus in a patient, wherein the method comprises administering to the patient in need of such treatment an effective amount of a compound according to claim 1, or a pharmaceutically acceptable salt or stereoisomer thereof.

17. A method for treating systemic lupus erythematosus in a patient, wherein the method comprises administering to the patient in need of such treatment an effective amount of the stereoisomer of the compound according to claim 8, or a pharmaceutically acceptable salt thereof.

18. A method for treating type 1 diabetes in a patient, wherein the method comprises administering to the patient in need of such treatment an effective amount of a compound according to claim 1, or a pharmaceutically acceptable salt or stereoisomer thereof.

19. A method for treating type 1 diabetes in a patient, wherein the method comprises administering to the patient in need of such treatment an effective amount of the stereoisomer of the compound according to claim 8, or a pharmaceutically acceptable salt thereof.

* * * * *